(12) United States Patent
Profy

(10) Patent No.: US 8,604,086 B2
(45) Date of Patent: Dec. 10, 2013

(54) SULFONIC ACID AND ALDEHYDE CONDENSATION POLYMERS FOR THE TREATMENT AND PREVENTION OF HPV

(75) Inventor: Albert T. Profy, Needham, MA (US)

(73) Assignee: Endo Pharmaceuticals Solutions Inc., Malvern, PA (US)

( * ) Notice: Subject to any disclaimer, the term of this patent is extended or adjusted under 35 U.S.C. 154(b) by 574 days.

(21) Appl. No.: 12/393,778

(22) Filed: Feb. 26, 2009

(65) Prior Publication Data
US 2009/0247639 A1  Oct. 1, 2009

Related U.S. Application Data

(60) Provisional application No. 61/031,906, filed on Feb. 27, 2008.

(51) Int. Cl.
*A61K 31/115*  (2006.01)
(52) U.S. Cl.
USPC ............ 514/694; 514/763; 514/765; 514/934
(58) Field of Classification Search
USPC .................................. 514/694, 763, 934, 765
See application file for complete search history.

(56) References Cited

U.S. PATENT DOCUMENTS

| 4,604,404 A | 8/1986 | Munson et al. |
| 5,614,559 A | 3/1997 | Singh et al. |
| 5,958,399 A | 9/1999 | Sonderfan et al. |
| 6,239,182 B1 | 5/2001 | Zaneveld et al. |

FOREIGN PATENT DOCUMENTS

WO    WO-94/03164    2/1994

OTHER PUBLICATIONS

Dohun Pyeon, et al.; *Production of Infectious Human Papillomavirus Independently of Viral Replication and Epithelial Cell Differentiation;* PNAS vol. 102, No. 26, pp. 9311-9316, Jun. 28, 2005.

*Primary Examiner* — Sreeni Padmanabhan
*Assistant Examiner* — Shobha Kantamneni
(74) *Attorney, Agent, or Firm* — RatnerPrestia

(57) ABSTRACT

The present invention relates to a method of treating and preventing a papillomavirus infection in an individual, comprising administering to the individual a therapeutically effective amount of a condensation polymer of an aromatic sulfonic acid and an aldehyde, or a pharmaceutically acceptable salt thereof.

19 Claims, 1 Drawing Sheet

Microbicidal activity of Pro2000 in the BPV-1-induced focus-forming assay

SULFONIC ACID AND ALDEHYDE CONDENSATION POLYMERS FOR THE TREATMENT AND PREVENTION OF HPV

CROSS REFERENCE TO RELATED APPLICATIONS

This application claims the benefit of the priority date of U.S. Provisional Patent Application No. 61/031,906, which was filed on Feb. 27, 2008, the disclosure of which is incorporated herein by reference in its entirety.

BACKGROUND OF THE INVENTION

Many condensation polymers of formaldehyde and aromatic sulfonic acids have been previously described. For instance, U.S. Pat. No. 4,604,404 discloses the use of such polymers as antiviral agents against the Herpes Simplex virus and HIV infection.

U.S. Pat. No. 5,614,559 discloses that condensation polymers of an aldehyde and aromatic sulfonic acids, such as formaldehyde naphthalene-sulfonic acid condensation polymers, can abrogate HIV gp120 binding to CD4, as demonstrated in CD4/gp120 binding assays. The use of this compound has been shown to be non-cytotoxic and non-inhibitory to antigen induced T lymphocyte proliferation. Based on these findings, these compounds were reported to be useful as therapeutic agents for the treatment and prevention of acquired immunodeficiency syndrome (AIDS), as well as AIDS-related complex (ARC), AIDS-related dementia and non-symptomatic HIV infection.

U.S. Pat. No. 5,958,399 discloses that condensation polymers of aromatic sulfonic acids and an aldehyde, such as naphthalene-sulfonic acid formaldehyde condensation polymers can inhibit or prevent pregnancy. However, none of these references teach or suggest the use of such condensation polymers in preventing or treating papillomavirus (PV) infection and related diseases or conditions.

The papillomaviruses (PVs) are a diverse group of non-enveloped DNA viruses that infect the skin and mucosal tissues of a range of vertebrate species, including humans. Animal PVs occur in a large number of species. Studies have developed bovine PV (BPV) and the Shope cottontail rabbit PV (RCPV) into model systems. Howett et al, *A Broad-Spectrum Microbicide with Virucidal Activity Against Sexually Transmitted Viruses*, Antimicrobial Agents and Chemotherapy, February 1999, p. 314-321.

Human papillomaviruses (HPVs) are double-stranded DNA viruses, which induce hyperproliferative lesions in epithelial tissues. HPVs cause warts in epithelial target tissues. Common warts of the hands, feet, and genital condylomata all represent common clinical infections of humans. See, Howett et al, supra. A group of genital mucosotropic HPV types are etiologic agents responsible for virtually all cases of cancer of the uterine cervix, as well as a substantial fraction of other ano-genital and head-and-neck cancers. Cancer associated genital HPV types, as well as another set of HPV types associated with the development of benign genital warts, are generally transmitted through sexual contact. Infection with genital HPV types is very common, with an estimated lifetime risk of infection of about 75%. Although most genital HPV infections are subclinical and self-limiting, a subset of persistently infected individuals have lesions that progress to premalignancy or cancer. Buck et al, *Carrageenan Is a potent Inhibitor of Papillomavirus Infection*, PloS Pathogens, July 2006, Volume 2, Issue 7, e. 69. A portion of persistent HPV infections can progress to invasive cervical cancer. Cervical cancer represents the second most frequent cause of cancer-related deaths in women, accounting for more than 200,000 deaths per year worldwide as of 2001. Christensen et al, *Papillomavirus Microbicidal Activities of High-Molecular-Weight Cellulose Sulfate, Dextran Sulfate, and Polysteyrene Sulfonate*, Antimicrobial and Chemotherapy, December 2001, p. 3427-3432.

Recent studies have suggested that condoms are, at best, only marginally effective in preventing the sexual transmission of HPV. Although highly effective prophylactic HPV vaccines are expected to become publicly available, they have possible drawbacks. The vaccines are relatively expensive and are likely to be PV type-restricted in their protection. Therefore the vaccines may not initially be available to women in all parts of the world and may not offer protection against all types of cancer-related HPV. See, Buck et al., supra. Compounds with microbicidal activity against papillomaviruses, therefore, may reduce incident infections and decrease the rates of cervical cancer. Thus there is a great need to develop such microbicides.

SUMMARY OF THE INVENTION

The present invention provides in one embodiment a method of preventing a papillomavirus infection in an individual, comprising administering to the individual a therapeutically effective amount of a condensation polymer of an aromatic sulfonic acid and an aldehyde, or a pharmaceutically acceptable salt thereof.

Another embodiment is a method of treating a papillomavirus infection in a papillomavirus-infected individual, comprising administering to the individual a therapeutically effective amount of a condensation polymer of an aromatic sulfonic acid and an aldehyde, or a pharmaceutically acceptable salt thereof.

The present invention further provides in another embodiment a method of inhibiting a papillomavirus infection comprising contacting the papillomavirus or warts caused by papillomavirus infection with a therapeutically effective amount of a condensation polymer of an aromatic sulfonic acid and an aldehyde, or a pharmaceutically acceptable salt thereof.

BRIEF DESCRIPTION OF THE DRAWING

FIG. 1 shows the microbicidal activity of an alkaline metal salt of a condensation polymer of an aromatic sulfonic acid and an aldehyde, PRO2000, in the BPV-1-induced focus-forming assay.

DETAILED DESCRIPTION

The preparation of aldehyde condensation polymers of aromatic sulfonic acids is generally known in the art. U.S. Pat. No. 4,604,404 exemplified methods of making them. In one embodiment, the polymers possess the general structure I:

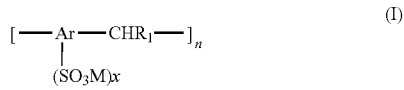

Aromatic sulfonic acids, as employed herein, include aromatic carbocyclic and heterocyclic rings substituted by one or more sulfonic acid moieties (e.g., x can be 1 to 4). Aromatic carbocyclic rings (Ar) include phenyl, naphthyl, tetrahydronaphthyl, biphenyl, phenylalkylphenyl, phenylalkenylphenyl, phenoxyphenyl, phenylthiophenyl and phenoxyalkoxyphenyl, for example. Aromatic heterocyclic rings (Ar) include, pyridinyl, pyrimidinyl, quinolinyl, thiophenyl, furanyl, pyrazolyl, imidazolyl, pyrrolyl and thiazolyl, for example.

Aldehydes (CHRO) useful in the preparation of compounds for the present invention include paraformaldehyde or formaldehyde, substituted or unsubstituted acetaldehyde, propionaldehyde and benzaldehyde, for example.

In one embodiment, the aldehyde is formaldehyde. Accordingly, $R_1$ of the formula can be hydrogen, substituted or unsubstituted alkyl (such as lower alkyl), substituted or unsubstituted aryl (such as phenyl). Substituents include, for example, alkyl, alkoxy, aryl, aryloxy, halogen, hydroxy, amino, alkylamino, dialkylamino, carboxyl, sulfonate and phosphonate.

The condensation polymer can be a free acid, ester or a pharmaceutically acceptable salt. M can be hydrogen, a pharmaceutically acceptable cation (e.g., an alkali metal, alkaline earth metal, or ammonium group), or a sulfonate blocking group, which can cleave or hydrolyze in vivo (e.g., a linear or branched alkyl). The term "polymer," as employed herein, includes any compound formed by the coupling of two or more monomers or repeating units (e.g., n is an integer of two or more). U.S. Pat. No. 4,604,404 exemplifies methods of preparing them.

In another embodiment, the polymer is the condensation product of a naphthalene sulfonic acid and formaldehyde of the formula (II):

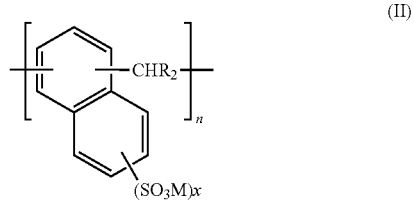

wherein x is 1 or 2; $R_2$ is hydrogen, alkyl, alkoxy or an anionic group, such as carboxyl and phosphonate; M is hydrogen or a pharmaceutically acceptable cation. In some instances, one or more of the sulfonic acid groups can be irreversibly blocked.

In one embodiment, the polymers include copolymers wherein the aldehyde and/or aromatic sulfonic acid are added as mixtures of different aldehydes and/or aromatic sulfonic acids (such as those defined above). Also included are copolymers wherein an aromatic group, not substituted by sulfonic acid, is added. For example, the aromatic group can be a carbocyclic or heterocyclic group (as defined above) unsubstituted or substituted by one or more groups, such as alkyl, alkoxy, aryl, aryloxy, halogen, hydroxy, sulfonamide, carboxyl or phosphonate.

In another embodiment, the molecular weight of the polymer (M.W.) is less than about 50 kDa. In another embodiment, the polymer's M.W. is less than about 50 kDa and greater than about 0.7 kDa. In yet another embodiment, the polymers are of a molecular weight between from about 1.3 to about 30 kDa, or between from about 4 to about 12 kDa. In one embodiment, the polymer is a 5±1 kDa condensate of 2-naphthalene sulfonic acid and formaldehyde.

In yet another embodiment, the average number of sulfonic acids per aromatic group is between about 0.5 to about 2.0. For instance, the average number of sulfonic acid per aromatic group can be about 1.0.

In one embodiment, the polymer is a condensation product of 2-naphthalene sulfonic acid and formaldehyde of formula III, wherein n is about 21 and M.W. is about 4 kDa to about 6 kDa., and the polydispersity (Mw/Mn) is less than 1.2.

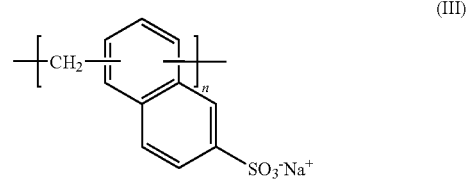

The narrow or mono-dispersed molecular weight polymers can be prepared by fractionation methods generally known in the art, such as solvent precipitation, gel permeation chromatography, salt precipitation and diafiltration. See, e.g., Polymer Fractionation, Editors, Cantow and Manfred, Jr., (Acad. Press) 1967. Alternatively, the polymers can be manufactured by the stepwise or controlled condensation of naphthalenesulfonic acid and formaldehyde. A "narrow-dispersed polymer" is defined as a polymeric composition wherein the species thereof possess substantially the same molecular weight. For example, a narrow-dispersed polymer includes polymeric compositions wherein the polydispersity is less than about 2, less than about 1.5, or less than about 1.2. A "mono-dispersed polymer" is defined as a polymeric composition wherein substantially all of the species thereof possess a single molecular weight, such as a tetramer, pentamer, hexamer, heptamer, octamer, nonamer, etc.

As described above, the condensation polymer can, optionally, be administered as a pharmaceutically acceptable salt. Examples of suitable salts include the alkaline, alkali metal and ammonium salts, such as calcium, sodium, potassium, ammonium and alkyl or aryl ammonium salts (such as trimethylammonium, triethylammonium and triethanolammonium (trolamine) salts).

One embodiment of this invention is a method of preventing a papillomavirus infection in an individual comprising administering to the individual a therapeutically effective amount of the preparation. Another embodiment is a method of treating a papillomavirus infection in a papillomavirus-infected individual comprising administering to the individual a therapeutically effective amount of the preparation. Yet another embodiment is a method of inhibiting a papillomavirus infection comprising contacting the papillomavirus or warts caused by papillomavirus infection with a therapeutically effective amount of the preparation. The papillomavirus may be a human papillomavirus (HPV) in any of the above described methods.

In any of the above described methods, the preparation or polymer can be administered intravaginally, rectally, or on genitalia in dosage formulations containing a physiologically acceptable vehicle and optional adjuvants and preservatives.

Formulations of the condensation polymers can be physiologically acceptable gels, foams and creams. Vehicles include saline sterile water, Ringer's solutions, and isotonic sodium chloride solutions. Exemplary vehicles include but are not limited to Sodium Chloride Injection USP (0.9%), Ringer's Injection USP, Lactated Ringer's Injection USP, Sodium Lactate Injection USP, Dextrose Injection USP (5% or 10%), Bacteriostatic Water for Injection USP and Sterile Water for Injection USP.

In one embodiment, the compound is composed in, applied to or sprayed on, e.g., as a film, a contraceptive device, such as a condom (including male condoms and female condoms, as in the REALITY female condom (Women's Health Company), see U.S. Pat. No. 4,735,621), or diaphragm.

In another embodiment, the formulation is a gel. Gelling agents for pharmaceutical formulations are generally known in the art. For example, the gelling agent can be hydroxyethyl cellulose (such as Hydroxyethyl Cellulose 250 HHX, (Natrosol)), guar gum, cellulose gum, crosslinked polyacrylic acid (such as, Carbopol 1342, Carbomer 974B, Carbomer 980, Carbomer 910, Carbomer 1382), or Theronic poloxymer. A typical gelling agent is Carbomer 1382, a copolymer of acrylic acid and a long chain methacrylate crosslinked with allylethers of pentaerythritol. The agent is generally added in an amount between about 1 to about 5% by weight.

The specific dosage level of active ingredient will depend upon a number of factors, including biological activity of the particular preparation and the general health of the patient or individual. In any of the above described methods, the polymer can be formulated at a concentration of between about 0.05% to about 10% by weight. In one embodiment, the polymer is present in a concentration between about 0.1% to about 7% by weight. In another embodiment, the polymer is present in a concentration between about 0.5% and about 2% by weight.

The formulation is generally administered prior to or after sexual intercourse (e.g., up to an hour before or twelve hours after intercourse), such as immediately prior to or after sexual intercourse (e.g., within 30 minutes before to one hour after intercourse). The compound can be administered overtly (with the consent of a male partner) or covertly (without the cooperation or consent of a male partner). Other regimens may be useful for the treatment of HPV infection. For example, daily application regardless of intercourse may be helpful for the treatment of HPV infection.

The preparation is administered in an amount which is effective to inhibit HPV infection. The preparation may be administered with other antiviral agents such as anti-HIV agents.

The preparation of the polymers of this invention can also be administered in conjunction with one or more contraceptive formulations, such as nonoxynol-9, octoxynol, chlorohexidine, benzalkonium chloride and menfegol.

EXAMPLES

The invention will be further illustrated by the following non-limiting examples.

Example 1

Synthesis of Condensates; Polymerization

Pursuant to the synthetic methods disclosed in U.S. Pat. No. 5,614,559, and U.S. Pat. No. 5,958,399. The following condensation polymers are prepared for use in the present invention:

TABLE 1

| Example | Product size (kDa) | | |
|---|---|---|---|
| | Mp | MWd | MW |
| 1* | 6.0 | 0.7-150 | 16 |
| 2* | 25 | 0.2-100 | 13 |
| 3* | 2.0 | 2-200 | 12 |
| 4* | 0.4 | 0.3-175 | 9 |
| 5 | 2.0 | 0.4-90 | 9 |

TABLE 1-continued

| Example | Product size (kDa) | | |
|---|---|---|---|
| | Mp | MWd | MW |
| 6 | 4.0 | 0.4-100 | 14 |
| 7 | 8.0 | 3-100 | 14 |
| 8 | 21 | 0.1-980 | 56 |
| 9 | 0.2 | 0.2-10 | 2 |
| 10 | 0.2 | 0.3-15 | 2 |
| 11 | 3.0 | 0.3-100 | 4 |
| 12 | 3.0 | 0.4-80 | 14 |
| 13 | 3.0 | 0.4-100 | 11 |
| 14 | 4.0 | 1-120 | 18 |

*Open vessel reactions;
Mp = peak molecular weight;
MWd = molecular weight distribution;
MW = molecular average weight Example 15

Synthesis of PRO2000 Condensation Polymer

The sodium salt of 2-naphthalene sulfonic acid (1000 g) was added to a glass reactor with 8925 ml ethanol, 3800 ml deionized water and 10 g of carbon. The mixture was heated to approximately 78° C. and filtered through Celite™. The mixture was cooled to ambient temperature and held for about 6 hours. The wet crystals were collected by filtration and dried in a vacuum oven (80° C./25" vacuum) to a constant weight. Average yield was 59%.

The recrystallized 2-naphthalene sulfonic acid (1000 g as prepared above) was then combined with water (866 g) and 99% sulfuric acid (330 ml). The reactor was sealed and heated with agitation to about 105° C. over a 130° C. oil bath. Formaldehyde (502 g, 37% aqueous solution) was added to the reactor over 45 minutes. The reactor was maintained for about 10 hours. Over the course of reaction, the internal pressure rose to about 11 psi.

After completion of the reaction, the contents of the reactor were cooled and diluted with 500 g of deionized water. The pH was adjusted from less than about 1 to a pH of about 7 by adding about 500 g NaOH. The reaction yielded at least about 90% unfractionated polymer.

The salts from the neutralization process were removed by fractionation by the addition of 10 l acetone, resulting in the formation of two layers. The lower layer was discarded. To the upper layer, 2 l of acetone were added, resulting again in two layers, the upper layer of which was discarded. About 600 g of water was added to the lower layer with about 1.4 l of acetone, again resulting in the formation of two layers. The lower layer was discarded, the upper layer transferred and treated with about 1.2 l of acetone. The upper layer formed was discarded and about 520 ml of water was added to the lower layer. The solution was concentrated and transferred to a vacuum oven and dried at 80° C./24" of vacuum to a constant weight. Fractionation was monitored by GPC/LS. The process yielded the condensation polymer, molecular weight between about 4000-6000 Daltons (average 11% yield).

Example 16

Preparation of PRO2000 Gel

The specified quantities of Example 15 (100 aqueous solution), purified water (USP), and lactic acid (1% aqueous solution (w/w)) were mixed thoroughly in the amounts set forth in Table 2. During mixing, the stated quantity of Carbomer 1382 (BF Goodrich, Cleveland, Ohio) was added and agitation was continued until the Carbomer was hydrated. A 50% aqueous solution (w/w) of Trolamine (Spectrum, New Brunswick, N.J.) was added, with mixing. The pH was monitored.

TABLE 2

| Reagent | Vehicle | Vehicle | 0.1% Gel | 0.5% Gel | 1.0% Gel | 4.0% Gel | 4.0% Gel |
|---|---|---|---|---|---|---|---|
| Formulation | 1 | 2 | 3 | 4 | 5 | 6 | 7 |
| Polymer (g) | none | none | 18.5 | 34.093 | 165.0 | 860.0 | 268.5 |
| Purified Water (g) | 6201.91 | 2548.0 | 1665.0 | 6234.26 | 1336.5 | 1096.5 | 5855.44 |
| Lactic Acid (g) (1% sol'n) | 3.60 | 140.0 | 92.6 | 3.64 | 82.5 | 107.5 | 3.60 |
| Carbomer 1.382 (g) | 63.0 | 56.01 | 37.09 | 86.4 | 33.0 | 43.01 | 126.0 |
| Trolamine (g) (50% sol'n) | 31.5 | 56.0 | 37.02 | 43.5 | 33.0 | 43.0 | 63.0 |
| pH (Initial) | — | 2.89 | 2.94 | — | 3.03 | 3.52 | — |
| pH (Final) | — | 4.73 | 4.93 | — | 4.66 | 4.60 | — |

The gels were filled into 5/8×3 inch epoxy-lined aluminum, blind end tubes with polypropylene caps and special No. 16 neck size (Montebello). The fill amount was approximately 3.7 g. The tubes were sealed And then sterilized in an autoclave at 121° C. for 20 minutes.

Example 17

Biological Activity

The potential irritant effects of 0.1%, 1% and 4% (Formulations 3, 5 and 6) concentrations of polymer, as formulated above, (PRO2000 gel) were evaluated in the vaginas of New Zealand White rabbits. Five rabbits in each of 5 groups received a daily 1-ml dose of PRO2000 gel, a vehicle gel (Formulation 2), or a 4% formulation of nonoxynol-9 (Conceptrol®; included for comparison) in the vaginal vault. The treatment was repeated for 14 consecutive days. One day after the last dose, rabbits were euthanized and the vaginal tissue was removed for histopathological evaluation. All rabbits exhibited no clinical signs of systemic toxicity nor external signs of irritation. Rabbits generally gained weight during the study. The histopathological irritation scores were graded as mild in each treatment group, and were well within the acceptable limits of this test.

Example 18

Effect of PRO2000 on BPV

The effect of the PRO2000 gels was studied on bovine papillomavirus (BPV) using the BPV-1 focus assay described in Howett et al, *A Broad-Spectrum Microbicide with Virucidal Activity against Sexually Transmitted Viruses*, Antimicrobial Agents and Chemotherapy, February 1999, p. 314-321.

BPV-1 focus assay: Cell-free stocks of BPV type 1 (BPV-1) were prepared by extraction (10% wt/vol) of epidermal bovine warts in PBS. In order to detect the transforming ability of BPV-1, C127 mouse cells were seeded into T-25 flasks ($3 \times 10^5$ cells per flask). After 24 hours of growth, sub-confluent cells were infected with BPV-1. For the positive controls, stock virus (20 µl) was diluted (1:1) with PBS, incubated at 37° C. for 10 minutes, diluted 1:1,000 and then added (100 µl) to the 5 ml of cell culture medium present on the cells. The cells were refed at 24 h and subsequently two times weekly. The presence of morphologically transformed foci was counted after 2 weeks and then again at 3 weeks. This assay was performed as described in Dvoretzky, I. et al 1980, *A quantitative in vitro focus assay for bovine papillomavirus*, Virology 103: 369-375.

Virus inactivations were carried out in vitro by the addition of concentrated PRO2000 solutions to the virus stocks (20 µl of virus plus 20 µl of PRO2000) and subsequent incubation at 37° C. for 10 or 30 minutes, as indicated. Following inactivation, virus was diluted 1:1,000 to lower the detergent concentration, and the preparation were immediately used for infection as described above. The microbicidal activity of PRO2000 in the BPV-1-induced focus-forming assay is shown in FIG. 1. The unit measurement on y-axis is the number of foci of morphologically transformed cells on the plate. Each focus represents a BPV-infected cell that has been transformed (i.e., made cancer-like). When plates of cells were treated with a set amount of cell-free BPV in the absence of PRO2000, about 70 foci were formed on each test plate. Low concentrations of PRO2000 did not affect this number. However, in the presence of higher PRO2000 concentrations the number of foci was reduced to zero, indicating that PRO2000 prevented infection. The increase in the number of foci seen at 10 micrograms/mL PRO2000 was probably aberrant. The data show that PRO2000 is effective at deactivating BPV cells at an $IC_{50}$ between about 10 and 100 µg/mL.

Example 19

Condom Compatibility of PRO2000

PRO 2000 gel (4%) was evaluated for compatibility with latex condoms. Using standard test methods, airburst and physical properties of non-lubricated, latex condoms ere evaluated immediately after unwrapping, or after exposure to 4% PRO2000 gel (30 minutes at 37° C., 95% relative humidity). The gel did not affect the properties of the condoms.

Example 20

Inhibition of HPV PsV Infection In Vitro

The ability of drugs to inhibit human papillomavirus (HPV) infection in vitro can be assessed using high-titer HPV gene transfer vectors known as pseudoviruses (PsV) [See, Refs 1-3, below]. The PsV can be constructed to model an HPV type of interest, such as HPV16, the type most commonly associated with cervical cancer in humans. The 293TT cell line (a human embryonic kidney cell line engineered to express high levels of SV40 T antigen) can be co-transfected with HPV capsid genes L1 and L2 together with a pseudogenome plasmid containing the SV40 origin of replication, leading to production of the HPV PsV, which can be purified by density gradient centrifugation. HPV PsV stocks can be designed to carry a reporter plasmid that provides a marker for infection (e.g., secreted alkaline phosphatase (SEAP) or green fluorescent protein (GFP)). To assess the ability of a drug to inhibit HPV infection, cells (e.g., 293TT or HeLa cells) can be plated, treated with serial dilutions of the drug of interest (for example, solutions of PRO2000 dissolved in the same culture medium that is used to grow 293TT or HeLa cells), treated with an appropriately diluted HPV PsV stock, and incubated for a suitable period of time (e.g., 24-60 hours, such as 36-48 hours). Tests are then performed for the marker of infection (e.g., SEAP activity in the culture supernatant; GFP by flow cytometry). The percentage of cells producing the marker at each dilution of drug can be plotted against the drug concentration to determine the 90% inhibitory dose ($IC_{90}$).

In an experiment of this type, it can be expected that PRO2000 will have an inhibitory effect on HPV infectivity of the test cells. Consistent with the results described for the microbicidal activity of PRO2000 in a BPV-1-induced focus-forming assay, PRO2000 can be expected to inhibit HPV16 PsV infection of the test cells at concentrations ranging from about 0.1 to about $10^4$ µg/mL, such as from about 1 to about $10^3$ µg/mL, from about 10 to about $10^2$ µg/mL, or from about 20 to about 50 µg/mL. At these concentrations of PRO2000 (i.e., µg of PRO 2000 per mL of total test cell culture), it is further expected that the percentage of test cells in the test cell culture, whose infection can be inhibited or prevented, will be found to be about 50% or greater, 75% or greater, 85% or greater, 90% or greater, or even 95%, or greater. In general, the higher the concentration of PRO2000 in the mixture or culture comprising the test cells—the higher the percentage of test cells in the mixture or culture, whose infection can be inhibited or prevented. Refs: [1] Buck C B, Pastrana D V, Lowy D R, Schiller J T (2004). Efficient Intracellular Assembly of Papillomaviral Vectors. J. Virol. 78: 751-757; [2] Buck C B, Pastrana D V, Lowy D R, Schiller J T (2005). Generation of HPV Pseudovirions Using Transfection and their Use in Neutralization Assays. Methods Mol. Med. 119: 445-462; and [3] Buck C B, Day P M, Thompson C D, Lubkowski J, Lu W, Lowy D R, Schiller J T (2006). Human Alpha-Defensins Block Papillomavirus Infection. Proc. Natl. Acad. Sci. USA 103: 1516-1521.

Example 21

Evaluation of the Effect of Drugs on HPV Infection in Humans

Drugs can be tested for their effects on the acquisition and course of HPV infection in humans. For example, a clinical trial could be conducted in which female volunteers at risk of HPV acquisition through sexual activity could, after providing informed consent, be randomly assigned to receive the drug of interest or a placebo. A dose of PRO2000 or placebo might be administered intravaginally, intrarectally, or on the genitalia (of the female or male), e.g., once daily, or before each act of sexual intercourse. Endocervical specimens could be collected periodically and tested for the presence of HPV by polymerase chain reaction (PCR) technology using L1 consensus primers and/or type-specific primers to determine the type(s) of HPV present. The effectiveness of PRO2000 could be determined by comparison of the proportion of women with incident HPV infection in the PRO2000 arm compared to the proportion with incident HPV infection in the placebo arm. It is expected that the proportion of women with incident HPV infection in the PRO2000 arm will be significantly lower than the proportion of women with incident HPV infection in the placebo arm.

In a particular embodiment of the invention, test subjects in the PRO2000 arm are instructed to apply a 2-gram dose of 0.5% PRO 2000 gel (equivalent to applying 10 mg of PRO2000 condensation polymer) intravaginally within 1 hour of the start of intercourse. Typically a 0.5% PRO2000 gel contains about 5000 µg (or 5 mg) PRO2000 per mL (1 mL of the gel is estimated to weigh about 1 gram). In one embodiment of the invention, about 0.5 to about 10 grams of the 0.5% PRO2000 gel is applied intravaginally, intrarectally, or topically, such as about 1 to about 5 grams, about 2 to about 5 grams, or about 2 to about 3 grams.

While the invention has been described in terms of preferred embodiments, it is apparent that other embodiments could be adopted or envisioned by one skilled in the art based on the disclosure provided above. Accordingly, it should be understood that the invention is not limited to the specific embodiments described, but rather the scope of the invention is to be limited only by the following claims.

I claim:

1. A method of inactivating a papillomavirus infection in an individual in need thereof, comprising administering to the individual a therapeutically effective amount of a condensation polymer of formula (III):

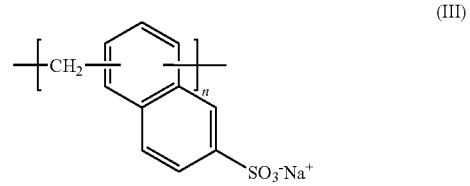

or a pharmaceutically acceptable salt thereof, wherein n is about 21.

2. The method according to claim 1, wherein the papillomavirus is human papillomavirus (HPV).

3. The method of claim 1, wherein the polymer is administered intravaginally, rectally or on genitalia.

4. The method of claim 1, wherein the condensation polymer is administered in a physiologically acceptable carrier.

5. The method of claim 4, wherein the physiologically acceptable carrier is a formulation selected from a gel, cream, and foam.

6. The method of claim 5, wherein the formulation is a gel.

7. The method of claim 5, wherein the condensation polymer is present in the formulation in a concentration between about 0.05% and about 10% by weight.

8. The method of claim 7, wherein the condensation polymer is present in the formulation in a concentration between about 0.1% and about 7% by weight.

9. The method of claim 8, wherein the condensation polymer is present in the formulation in a concentration of about 0.5% or about 2% by weight.

10. A method of treating a papillomavirus infection in a papillomavirus-infected individual in need thereof, comprising administering to the individual a therapeutically effective amount of a condensation polymer of formula (III):

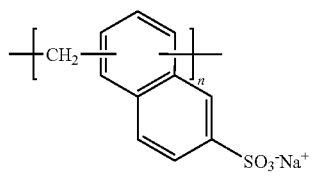

or a pharmaceutically acceptable salt thereof, wherein n is about 21.

11. The method according to claim 10, wherein the papillomavirus is human papillomavirus (HPV).

12. The method of claim 10, wherein the condensation polymer is administered intravaginally, rectally, or on genitalia.

13. The method of claim 10, wherein the condensation polymer is administered in a physiologically acceptable carrier.

14. The method of claim 13, wherein the physiologically acceptable carrier is a formulation selected from a gel, cream, and foam.

15. The method of claim 14, wherein the formulation is a gel.

16. The method of claim 14, wherein the condensation polymer is present in the formulation in a concentration between about 0.05% and about 10% by weight.

17. The method of claim 16, wherein the condensation polymer is present in the formulation in a concentration between about 0.1% and about 7% by weight.

18. The method of claim 17, wherein the condensation polymer is present in the formulation in a concentration of about 0.5% or about 2% by weight.

19. A method of inactivating a papillomavirus infection in an individual in need thereof, comprising contacting the papillomavirus or warts caused by papillomavirus infection with a therapeutically effective amount of a condensation polymer of formula (III):

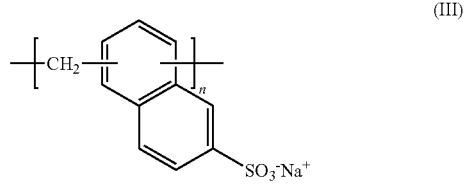

or salt thereof, wherein n is about 21.

* * * * *